US009234896B2

(12) United States Patent
Klock et al.

(10) Patent No.: US 9,234,896 B2
(45) Date of Patent: Jan. 12, 2016

(54) METHOD FOR MANUFACTURING SPECIFIC BINDING MOLECULES AGAINST SELECTED TARGET MOLECULES, KIT, AND BINDING MOLECULES

(75) Inventors: Gerd Klock, Dieburg (DE); Dirk Kaiser, Eppertshausen (DE); Mark Andre Freyberg, Darmstadt (DE)

(73) Assignee: CYTOTOOLS AG, Darmstadt (DE)

( * ) Notice: Subject to any disclaimer, the term of this patent is extended or adjusted under 35 U.S.C. 154(b) by 1797 days.

(21) Appl. No.: 11/579,081

(22) PCT Filed: Apr. 29, 2005

(86) PCT No.: PCT/EP2005/004604
§ 371 (c)(1),
(2), (4) Date: Oct. 30, 2006

(87) PCT Pub. No.: WO2005/108602
PCT Pub. Date: Nov. 17, 2005

(65) Prior Publication Data
US 2008/0003563 A1    Jan. 3, 2008

(30) Foreign Application Priority Data

Apr. 30, 2004   (DE) .................. 10 2004 021 707

(51) Int. Cl.
*C40B 30/04* (2006.01)
*G01N 33/68* (2006.01)
*C12N 15/11* (2006.01)
*C12N 15/115* (2010.01)

(52) U.S. Cl.
CPC .......... *G01N 33/6845* (2013.01); *C12N 15/111* (2013.01); *C12N 15/115* (2013.01); *C12N 2310/16* (2013.01); *C12N 2310/322* (2013.01); *C12N 2320/11* (2013.01); *C12N 2330/31* (2013.01); *C40B 30/04* (2013.01)

(58) Field of Classification Search
None
See application file for complete search history.

(56) References Cited

U.S. PATENT DOCUMENTS

| | | | | |
|---|---|---|---|---|
| 5,475,096 | A | 12/1995 | Gold et al. | 536/23.1 |
| 5,670,637 | A | 9/1997 | Gold et al. | 536/22.1 |
| 5,756,291 | A * | 5/1998 | Griffin et al. | 435/6 |
| 6,001,988 | A | 12/1999 | Parma et al. | 536/24.3 |
| 6,329,145 | B1 | 12/2001 | Janjic et al. | 435/6 |
| 7,282,556 | B2 * | 10/2007 | Parkos | 530/327 |
| 2006/0257866 | A1 * | 11/2006 | Welch et al. | 435/6 |

FOREIGN PATENT DOCUMENTS

WO    WO 96/34875    11/1996

OTHER PUBLICATIONS

Bridonneau et al ( J. Med. Chem. 1998, 41, 778-786)(II).*
Jenison (Science, 263, 1994, p. 1425).*
Arap et al., "Steps Toward Mapping the Human Vasculature by Phage Display," *Nature Medicine*, 8(2):121-127 (2002).
Azriel-Rosenfeld et al., "A Human Synthetic Combinatorial Library of Arrayable Single-chain Antibodies Based on Shuffling in Vivo Formed CDRs into General Framework Regions," *J. Mol. Biol.*, 335:177-192 (2004).
Baselga, "The EGFR as a Target for Anticancer Therapy-focus on Cetuximab," *Eur. J. Cancer*, 37:S16-S22 (2001).
Berliner et al., "Activated Polymorphonuclear Leukocytes and Monocytes in the Peripheral Blood of Patients with Ischemic Heart and Brain Conditions Correspond to the Presence of Multiple Risk Factors for Atherothrombosis," *Cardiology*, 94:19-25 (2000).
Birnboim et al., "A Rapid Alkaline Extraction Procedure for Screening Recombinant Plasmid DNA," *Nucleic Acids Research*, 7(6):1513-1523 (1979).
Blackwell et al., "A One-bead, One-stock Solution Approach to Chemical Genetics: Part 1," *Chemistry & Biology*, 8:1167-1182 (2001).
Blank et al., "Systematic Evolution of a DNA Aptamer Binding to Rat Brain Tumor Microvessels," *J. Biol. Chem.*, 276(19):16464-16468 (2001).
Bridonneau et al., "Site-directed Selection of Oligonucleotide Antagonists by Competive Elution," *Antisense & Nucleic Acid Drug Development*, 9:1-11 (1999).
Clemons et al., "A One-bead, One-stock Solution Approach to Chemical Genetics: Part 2," *Chemistry & Biology*, 8:1183-1195 (2001).
Cohen, "Overview: Mechanisms of Apoptosis," *Immunology Today*, 14(3):126-130 (1993).
Daniels et al., "A Tenascin-C Aptamer Identified by Tumor Cell SELEX: Systematic Evolution of Ligands by Exponential Enrichment," *PNAS*, 100(26):15416-15421 (2003).
Davies et al., "Effects of Cytochalasin B on Endocytosis and Exocytosis," *Frontiers of Biology*, 46:143-160 (1978).
den Broeder et al., "Long Term Anti-tumour Necrosis Factor ☐ Monotherapy in Rheumatoid Arthritis: Effect on Radiological Course and Prognostic Value of Markers of Cartilage Turnover and Endothelial Activation," *Ann. Rheum. Dis.*, 61:311-318 (2002).
Doucet et al., "Interleukin (IL) 4 and IL-13 Act on Human Lung Fibroblasts," *J. Clin. Invest.*, 101(10):2129-2139 (1998).
Dudez et al., "Characterization of a Novel Chemotactic Factor for Neutrophils in the Bronchial Secretions of Patients with Cystic Fibrosis," *J. Infections Dis.*, 186:774-781 (2002).

(Continued)

*Primary Examiner* — Christian Boesen
(74) *Attorney, Agent, or Firm* — Marshall, Gerstein & Borun LLP

(57) ABSTRACT

A method for the isolation of specific molecules which bind highly selectively to chosen target molecules. In particular, due to displacement with a specific competitor, binding molecules are selected which preferably bind to previously known epitopes.

19 Claims, No Drawings

(56) References Cited

OTHER PUBLICATIONS

Feldmann et al., "Rheumatoid Arthritis," *Cell*, 85:307-310 (1996).
Fellouse et al., "Bacteriophage That Display Small Molecules," *Chemistry & Biology*, 10:783-786 (2003).
Fitzwalter et al., "A SELEX Primer," *Methods in Enzymology*, 267:275-301 (1996).
Freyberg et al., "Proatherogenic Flow Conditions Initate Endothelial Apoptosis via Thrombospondin-1 and the Integrin-associated Protein," *Biochem. Biophy. Res. Comm.*, 286:141-149 (2001).
Galbraith et al., "Metabolic and Cytoskeletal Modulation of Transferrin Receptor Mobility in Mitogen-activated Human Lymphocytes," *Clin. Exp. Immun.*, 42(2):285-293 (1980).
Giri et al., "β-Amyloid-induced Migration of Monocytes Across Human Brain Endothelial Cells Involves RAGE and PECAM-1," *Am. J. Physiol. Cell Physiol.*, 279:C1772-C1781 (2000).
Heyman et al., "Genome-scale Cloning and Expression of Individual Open Reading Frames Using Topoisomerase I-Mediated Ligation," *Genome Research*, 9:383-392 (1999).
Homann et al., "Combinatorial Selection of High Affinity RNA Ligands to Live African Trypanosomes," Nucleic Acids Research, 27(9):2006-2014 (1999).
Hornick et al., "Single Amino Acid Substitution in the Fc Region of Chimeric TNT-3 Antibody Accelerates Clearance and Improves Immunoscintigraphy of Solid Tumors," *J. Nucl. Med.*, 41:355-362 (2000).
Hummel et al., "Production of MMPs in Human Cerebral Endothelial Cells and Their Role in Shedding Adhesion Molecules," *J. Neuro. Exp. Neurol.*, 60(4):320-327 (2001).
Irvine et al., "Selexion: Systematic Evolution of Ligands by Exponential Enrichment with Integrated Optimization by Non-linear Analysis," *J. Mol. Biol.*, 222:739-761 (1991).
Jayasena, "Aptamers: An Emerging Class of Molecules That Rival Antibodies in Diagnostics," *Clinical Chemistry*, 45(9):1628-1650 (1999).
Johnstone et al., "A Central Role for Astrocytes in the Inflammatory Response to β-amyloid; Chemokines, Cytokines and Reactive Oxygen Species are Produced," *J. Neuroimmunology*, 93:182-193 (1999).
Kaplan et al., "Temperature Shifts Induce the Selective Loss of Alveolar-Macrophage Plasma Membrane Components," *J. Cell Biol.*, 94:12-19 (1982).
Khandurina et al., "Microchip-based High-throughput Screening Analysis of Combinatorial Libraries," *Curr. Opin. Chem. Biol.*, 6:359-366 (2002).
Krein et al., "Roles for Insulin-like Growth Factor I and Transforming Growth Factor-β in Fibrotic Lung Disease," *Chest*, 122(6):289S-293S (2002).
Lamla et al., "Searching Sequence Space for High-affinity Binding Peptides Using Ribosome Display," *J. Mol. Biol.*, 329:381-388 (2003).
Larche et al., "The Role of T Lymphocytes in the Pathogenesis of Asthma," *J. Allergy Clin. Immunol.*, 111(3):450-463 (2003).
Lentsch et al., "Regulation of Inflammatory Vascular Damage," *J. Pathology*, 190:343-348 (2000).
Lenz et al., "Chemical Ligands, Genomics and Drug Discovery," *DDT*, 5(4):145-156 (2000).
Lyons et al., "Cleavage of Membrane-associated ICAM-1 From Astrocytes," *GLIA*, 22:103-112 (1998).
MacBeath et al., "Printing Proteins as Microarrays for High-throughput Function Determination," *Science*, 289:1760-1763 (2000).
Martell et al., "Optimizing Aptamer Activity for Gene Therapy Applications Using Expression Cassette SELEX," *Mol. Ther.*, 6(1):30-34 (2002).
Métézeau et al., "Endocytosis of the Membrane Immunoglobulins of Mouse Spleen B-cells: A Quantitative Study of its Rate, Amount and Sensitivity to Physiological, Physical and Cross-linking Agents," *EMBO J.*, 3(10):2235-2242 (1984).
Mukae et al., "Elevated Levels of Circulating Adhesion Molecules in Patients with Active Pulmonary Tuberculosis," *Respirology*, 8:326-331 (2003).
Murakami et al., "Macrophage Migration Inhibitory Factor Activates Antigen-presenting Dendritic Cells and Induces Inflammatory Cytokines in Ulcerative Colitis," *Clin. Exp. Immunol.*, 128:504-510 (2002).
Nielson et al., "Monoclonal Antibody to Human 66 000 Molecular Weight Plasminogen Activator From Melanoma Cells. Specific Enzyme Inhibition and One-step Affinity Purification," *EMBO J.*, 2(1):115-119 (1983).
Nord et al., "Recombinant Human Factor VIII-specific Affinity Ligands Selected from Phage-displayed Combinatorial Libraries of Protein A," *Eur. J. Biochem.*, 268:4269-4277 (2001).
Parker et al., "Soluble Adhesion Molecules and Unstable Coronary Artery Disease," *Atherosclerosis*, 156:417-424 (2001).
Pecheur et al., "Integrin αvβ3 Expression Confers on Tumor Cells a Greater Propensity to Metastasize to Bone," *FASEB J.*, (2002).
Pelsers et al., "A Sensitive Immunoassay for Rat Fatty Acid Translocase (CD36) Using Phage Antibodies Selected on Cell Transfectants: Abundant Presence of Fatty Acid Translocase/CD36 in Cardiac and Red Skeletal Muscle and Up-regulation in Diabetes," *Biochem. J.*, 337:407-414 (1999).
Rhodes et al., "The Generation and Characterization of Antagonist RNA Aptamers to Human Oncostatin M," *J. Biol. Chem.*, 275(37):28555-28561 (2000).
Ribatti et al., "Angiogenesis and Anti-angiogenesis in Neuroblastoma," *Eur. J. Cancer*, 38:750-757 (2002).
Schmidt et al., "Interleukin-12 Antagonists as New Therapeutic Agents in Inflammatory Bowel Disease," *Pathobiology*, 70:177-183 (2003).
Schram et al., "Vascular Risk Factors and Markers of Endothelial Function as Determinants of Inflammatory Markers in Type 1 Diabetes," *Diabetes Care*, 26(7):2165-2173 (2003).
Shuman, "Novel Approach to Molecular Cloning and Polynucleotide Synthesis Using Vaccina DNA Topoisomerase," *J. Biol. Chem.*, 269(51):32678-32684 (1994).
Woiwode et al., "Synthetic Compound Libraries Displayed on the Surface of Encoded Bacteriophage," *Chemistry & Biology*, 10:847-858 (2003).
Xu, "Role of Heat Shock Proteins in Atherosclerosis," *Arterioscler Thromb Vasc. Biol.*, 22:1547-1559 (2002).
Zhou et al., "Recombinant Antibody Fab Against the Hypervariable Region 1 of Hepatitis C Virus Blocks the Virus Absorption to Susceptible Cells in Vitro," *Antiviral Research*, 56:51-59 (2002).
International Search Report for International Application No. PCT/EP2005/004604, dated Aug. 31, 2005.

\* cited by examiner

SEQUENCE LISTING

```
<160> NUMBER OF SEQ ID NOS: 3

<210> SEQ ID NO 1
<211> LENGTH: 47
<212> TYPE: DNA
<213> ORGANISM: Artificial Sequence
<220> FEATURE:
<223> OTHER INFORMATION: Synthetic nucleotide

<400> SEQUENCE: 1
gcgaagcttt aatacgactc actataggga gacgatattc gtccatc        47

<210> SEQ ID NO 2
<211> LENGTH: 24
<212> TYPE: DNA
<213> ORGANISM: Artificial Sequence
<220> FEATURE:
<223> OTHER INFORMATION: Synthetic nucleotide

<400> SEQUENCE: 2
ggtcgagaat tcagtcggac agcg        24

<210> SEQ ID NO 3
<211> LENGTH: 79
<212> TYPE: DNA
<213> ORGANISM: Artificial Sequence
```

```
-continued

<220> FEATURE:
<223> OTHER INFORMATION: Synthetic nuclelotide
<220> FEATURE:
<221> NAME/KEY: misc_feature
<222> LOCATION: (19)..(58)
<223> OTHER INFORMATION: n is a, c, g, or t

<400> SEQUENCE: 3
gaattcagtc ggacagcgnn nnnnnnnnnn nnnnnnnnnn nnnnnnnnnn nnnnnnnnga    60
tggacgaata tcgtctccc                                                79
```

METHOD FOR MANUFACTURING SPECIFIC BINDING MOLECULES AGAINST SELECTED TARGET MOLECULES, KIT, AND BINDING MOLECULES

BACKGROUND OF THE INVENTION

1. Field of the Invention

The invention relates to a method for the isolation of specific molecules which bind highly selectively to chosen target molecules.

2. Related Technology

Today, a series of different methods are available for the identification of biochemical molecules such as peptides, antibodies, nucleic acids or synthetic-chemical substances which are to be developed for diagnostic or therapeutic purposes. In this connection, modern research work related to finding new active substances, has largely concentrated on the use of molecule libraries. In these libraries, biomolecules are made available—often in very large numbers, i.e. between $10^9$ and $10^{15}$ of different species. In the ideal case, these libraries can be searched using different high throughput methods (Lenz, G. R. et al. (2000) Drug Discovery Today 5(4) 145-156; Jayasena, S. D. (1999). Clin. Chem. 45(9): 1628-1650; Khandurina, J. and A. Guttman (2002). Curr. Opin. Chem. Biol. 6(3), 359-366).

Such relatively new methods are already used in the preliminary searches for new active substances, e.g. for the functional characterisation of newly discovered proteins including the identification of their binding partners (MacBeath, G. and S. L. Schreiber (2000) Science 289(5485), 1760-1763). Screening methods involving molecule libraries are especially important for finding active substances which are identified by their binding to target proteins (target molecules). In this connection, there are libraries for macromolecules such as peptides or nucleic acids (aptamers) and combinatorial libraries of small organic molecules (Azriel-Rosenfeld, R. et al. (2004) J. Mol. Biol. 335(1): 177-192; Jayasena, S. D. (1999). Clin. Chem. 45(9): 1628-1650;; Khandurina, J. and A. Guttman (2002). Curr. Opin. Chem. Biol. 6(3), 359-366; MacBeath, G. and S. L. Schreiber (2000) Science 289(5485), 1760-1763).

Endothelial and immune cells play a central role in a large number of disorders and are often involved as causative factors in disease development. Here, very often, the decisive factors involved are the membrane molecules present on the cell surface whose function is activated by specific ligands. Here, below, a few examples are given to illustrate this:

Asthma: Cell activation and the aggravation of inflammation by specific interleukins has been observed in asthma (Doucet, C., D. Brouty-Boye, et al. (1998) J. Clin. Invest. 101(10): 2129-2139 ; Larche, M., D. S. Robinson, et al. (2003) J. Allergy Clin. Immunol. 111(3): 450-463.

Mucoviscidosis (cystic fibrosis): Chronic inflammation of the respiratory system is aggravated by stimulating factors (Dudez, T. S., M. Chanson, et al. (2002) J. Infect. Dis. 186(6): 774-781).

Fibrotic Lung Disease: Sustained inflammatory reactions lead to the release of growth factors which cause increased cell division (Krein, P. M. and B. W. Winston (2002) Chest 122(6 Suppl): 289S-293S).

Morbus Crohn and Ulcerative Colitis: In both intestinal affections, certain cytokines, by binding their receptors to the cell surface, promote the inflammatory processes (Schmidt, C., T. Marth, et al. (2002) Pathobiology 70(3): 177-83; Murakami, H., S. M. Akbar, et al. (2002) Clin. Exp. Immunol. 128(3): 504-510.)

Atherothrombosis in Diabetes patients: Diabetes is a risk factor for atherothrombosis and other vascular diseases whereby inflammation markers on immune cells and adhesion factors play a causative role (Berliner, S., O. Rogowski, et al. (2000) Cardiology 94(1): 19-25; Schram, M. T., N. Chaturvedi, et al. (2003) Diabetes Care 26(7), 2165-2173).

Rheumatoid arthritis: The disease is considered to be a chronic inflammatory process whereby the immune response stimulating and inhibiting factors are out of balance (Feldmann, M., et al. (1996) Cell 85(3): 307-310; den Broeder, A. A. et al. (2002) Ann. Rheum. Dis. 61(4): 311-318).

Cancer: Processes such as cell growth, angiogenesis, and the metastatic spread of tumors require the interaction of membrane receptors of the tumor cells with specific ligands (Baselga J. (2001) Eur. J. Cancer 37 suppl 4: P16-P22; Ribatti, D., A. Vacca, et al. (2002) Eur. J. Cancer 38(6): 750-757 ; Pecheur, I., O. Peyruchaud, et al. (2002) Faseb J. 16(10): 1266-1268).

Arteriosclerosis: A large number of membrane receptors play a decisive part in the development of arteriosclerosis (Freyberg, M. A., D. Kaiser, et al. (2001) Biochem. Biophys. Res. Commun. 286(1): 141-149; Lentsch, A. B. and P. A. Ward (2000) J. Pathol. 190(3): 343-348; Parker, C., 3rd, J. A. Vita, et al. (2001). Atherosclerosis 156(2): 417-424; Xu, Q. (2002) Arterioscler. Thromb. Vasc. Biol. 22(10): 1547-1559).

Alzheimer's Disease: In patients with Alzheimer's disease, the amyloid beta-protein can initiate an immune reaction in the brain which contributes to the course of the disease (Giri, R., Y. Shen, et al. (2000) Am. J. Physiol. Cell Physiol. 279(6): C1772-81; Johnstone, M., A. J. Gearing, et al. (1999) J. Neuroimmunol. 93(1-2): 182-193).

Today, many of these conditions are still very difficult or even impossible to treat successfully. In many cases, this is due to the fact that, as a rule, in spite of the substance libraries discussed above, faster and more sensitive screening methods and the recombinant manufacturing of target molecules, it has not been possible to isolate binding molecules which, under in vivo conditions, are highly effective and which have a strong binding to the chosen target molecule.

In this expert field therefore, there is still a great necessity for the development of active substances for medically relevant target molecules. Here, in almost all cases, the therapeutic effect is first mediated by the binding of the active substance to the medically relevant target molecule.

In particular, experience has shown that the screening methods employed with the current status of technology are rarely successful in isolating good binding molecules for native cell membrane molecules—and even then only with the greatest of difficulty. Here, the inclusion of the cell surface in the active substance development is particularly important because, using the methods to date, if at all, overwhelmingly binders against intracellular proteins or extracellular soluble proteins have been able to be isolated.

Among the problems here, there is the necessarily high cost for the isolation of the target molecules proteins as well as the fact that the isolated membrane proteins are possibly then present is the screening procedure in a changed structure. This would then no longer correspond with the in vivo situation, and thus the isolated binding molecules would demonstrate—if any at all—a reduced efficacy in vivo—in comparison with the experimental situation.

Previously published status of technology selection methods on mammalian cells (Arap, W., M. G. Kolonin, et al. (2002) Nat. Med. 8(2): 121-127; Blank, M., T. Weinschenk, et al. (2001) J. Biol. Chem. 276(19): 16464-16468; Daniels, D. A., H. Chen, et al. (2003) Proc. Natl. Acad. Sci. U.S.A. 100(26): 15416-15421) were carried out with the purpose of first of all obtaining a wide spectrum of binding molecules (aptamers, peptides). These should then cover a large part of the surface proteins of the cell in question, e.g. a tumor cell, as targets. The only other additional option here, during the process or subsequently, would be to carry out a counter selection with a control cell (here not a tumor cell) in order to trap as many binding molecules as possible on this control cell and thus eliminate them. After this, in a high expenditure process, the target protein belonging to every binding molecule obtained must be searched for. Because however, today, many target proteins which have a medical relevance are already known, then these methods for finding an active substance against a protein which is already known are, in most cases, far too expensive. The applicability with a complete synthetic-chemical library (single pool) is, up to now, practically limited-to one technical principle: the specific binding to interesting targets remains limited to soluble proteins which can be first offered to the synthetic molecules as binding partners after expression and purification.

As yet, effective substances can only be identified as individual compounds on living cells but not in a "pool." This means that, especially here, binding tests are currently only possible as purely analytical tests in the form of numerous individual tests. The same applies to functional tests on cells where e.g. the modulation of cellular functions, such as cell division or the uptake of certain substances in the cell is carried out with a high workload for each individual substance, i.e. only in an analytical form but not as a preparative selection procedure from a pool of substances. As with other methods for the identification of substances from substance libraries (antibody, phage display, peptide and nucleic acid (aptamer) libraries), there is therefore, even for the highly promising synthetic chemical libraries, as yet no method which can be applied to the large number of potential target proteins on cell surfaces, usually receptors in cell membranes.

Therefore, according to the state of the art, there is an immense need for improved methods with whose help a large number of membrane proteins, which are associated with the origination of disease, can be made accessible to the modem methods of active substance development.

GENERAL DESCRIPTION OF THE INVENTION

The invention therefore provides a method with which specific binding molecules can be manufactured or isolated against selected native target molecules. In particular, the method should enable the highly selective isolation of binding molecules against selected native target molecules, i.e. specifically only targeting one single target molecule, excluding a maximum of nonspecifically binding molecules without isolating the actual target molecule, including such target molecules with low copy numbers and such which e.g. are internalised after ligand formation through endocytosis.

According to the inventive method, a substance library containing potential binding molecules is produced and brought into contact with the target molecules,
  a nonspecific binding competitor is added,
  at least one washing process is carried out,
  a specific binding competitor for the selected target molecule in a concentration of at least about 10 times, preferably at least about 100 times, particularly preferably about 1,000 times higher than the dissociation constant $K_D$ (M) of the pair consisting of specific binding competitor and target molecule in the substance library is added and incubated, and the now separated specific binding molecules, using a suitable method chosen for the substance library, are isolated and/or if necessary amplified.

In a preferred embodiment, the substance library is an amplifiable substance library selected from the group consisting of nucleic acid libraries, phage display-libraries, antibody libraries, peptide libraries and synthetic-chemical libraries, as are well known in this expert field, and which are easy to produce according to the published methods well-known in this field. If necessary, such a substance library can be purchased.

As the method according to the invention can in principle be carried out both for amplifiable as well as for non-amplifiable substance libraries, in step a), various libraries can be used. These can be either obtained from the market or can be easily manufactured using the well known methods of the status of technology.

In a further preferred embodiment, steps a) and b) of the method described above can be carried out simultaneously.

In a further preferred embodiment, the nonspecific competitor is chosen from the group consisting of milk powder, serum proteins such as serum albumin or nucleic acids such as tRNA or yeast-RNA, erythrocytes, erythrocyte ghosts (membrane skeletons), cell lines of haematopoietic origin, such as lymphoma or leukaemia cells, and HeLa suspension cells, as well as cell organelles such as cell nuclei or mitochondria, whereby the cells, cell membranes or organelles do not carry the target molecule, preferred here are erythrocytes, erythrocyte ghosts (membrane skeletons), cell lines of haematopoietic origin, such as lymphoma or leukaemia cells, or HeLa suspension cells, as well as cell organelles such as cell nuclei or mitochondria, whereby the cells, cell membranes or organelles do not carry the target molecule.

Especially preferred as the nonspecific competitor are erythrocytes and/or erythrocyte ghosts (membrane skeletons) which do not carry the target molecule.

In a further preferred embodiment, the steps a) to d) are repeated, preferably not more than three times to five times following after each other, whereby from the second round onwards, the binding molecules obtained in step e) are used in step a) instead of the amplifiable library.

In a further preferred embodiment, the library used is an aptamer library. Methods for manufacturing such aptamer libraries are well known and generally originate from the U.S. Pat. No. 5,475,096 where corresponding methods are revealed. These methods were further developed and are available to experts in an overwhelming number of variations.

In a further preferred embodiment, the target molecules in step a) of the method according to the invention are in a native condition, in particular compounded with a biomembrane, preferably on the surface of a cell membrane, particularly preferably on intact cells.

In a further preferred embodiment, in step a), an endocytosis inhibitor is added in a sufficient volume to inhibit endocytosis, preferably cytochalasin B in a volume of 1 μM to 10 μM.

In a further preferred embodiment, the selected target molecule is a membrane-bound molecule, which is also known in a soluble form, and in step a) a proteinase inhibitor is added.

In a further preferred embodiment, the specific binding competitor is selected from the group consisting of antibodies and their fragments, aptamers, and ligands of the target molecules as well as low-molecular competitors.

Here, especially preferably, the specific binding competitors consist of ligands for clinical or diagnostic use or other interesting surface molecules of cells. Especially preferred here are IAP or αvβ3.

It is especially advantageous that just such binding molecules can be manufactured with the method according to the invention, which specifically disturb the interaction between ligand and target molecule and thus, in comparison with the methods known in the status of technology, there is a strongly increased probability of obtaining functional binders, i.e. those which imitate or inhibit the interaction of the e.g. natural ligand with the target molecule. Thus, in this way, in a surprisingly fast and simple manner, it is possible to manufacture biologically active binding molecules and thus potential active substances.

In a further preferred embodiment the invention relates to a kit of parts comprising of at least one nonspecific binding competitor and an endocytosis inhibitor and/or a protease inhibitor. The kit of parts can also contain an amplifiable substance library.

Furthermore, the invention relates to those binding molecules which were isolated using the method according to the invention as well as their application—e.g. in therapy or diagnosis.

For the purposes of the invention, an amplifiable substance library is preferably understood as a library selected from the group consisting of nucleic acid library, phage display-library, antibody library or synthetic-chemical library.

Therefore, according to the invention, under "specific binding molecules" such molecules are understood which are the objects of numerous substance libraries already manufactured according to the status of technology. Among these, for example, are aptamers, antibodies or their fragments, peptides, anticalins and chemically synthesised molecules.

Therefore, the potential binding molecule for isolation results automatically from the type of manufactured and selected substance library.

The specific binding competitor, which has an affinity to the target protein, is best selected from the group consisting of antibodies, antibody fragments, peptides, DNA and RNA aptamers, low-molecular compounds and others such as naturally occurring ligands of the target protein.

This specific binding competitor, depending on its affinity to the target molecule, is used at a concentration of at least 1 μM, preferably of at least 10 μM, especially preferably of at least 100 μM, very especially preferably of at least and most preferably of all of at least 10 mM. It goes without saying, however, that this concentration, due to the availability and/or the solubility of the specific binding competitor, must have an upper limit which can be very easily determined in each case by an expert.

Here, the expert, within the scope of the experimental possibilities, will prefer to use a high concentration of specific binding competitor. Of course, nothing is known about the affinity of the potential binding molecule from the substance library before the experiment is carried out. In general, preferably strong binders should be isolated so that a possibly high concentration of specific binding competitor is desirable.

If the binding constant of the specific competitor for the target molecule is known or can at least be estimated, then the concentration of the binding competitor lies at least about 10 times, preferably at least about 100 times, especially preferably at least about 1000 times higher than the value of the known, calculated or estimated binding constant ($K_D$).

Known values for binding constants ($K\{D\}$) of the binding of antibodies or antibody fragments to proteins are e.g. $10^{-10}$, to $10^{-8}$ M (Homick, J. L., J. Sharifi, et al. (2000) J. Nucl. Med. 41(2): 355-362; Nielsen, L. S., J. G. Hansen, et al. (1983) Embo J. 2(1): 115-119; Zhou, Y. H., M. Takekoshi, et al. (2002) Antiviral Res. 56(1): 51-59), for aptamers $10^{-9}$ to $10^{-7}$ M (Rhodes, A., A. Deakin, et al. (2000) J. Biol. Chem. 275 (37): 28555-28561; Martell, R. E., J. R. Nevins, et al. (2002) Mol. Ther. 6(1): 30-34) or for peptides $10^{-5}$ to $10^{-8}$ M (Lamla, T. and V. A. Erdmann (2003) J. Mol. Biol. 329(2): 381-388; Nord, K., O. Nord, et al. (2001) Eur. J. Biochem. 268(15): 4269-4277).

In a further preferred embodiment the invention relates to a kit of parts comprising of at least one nonspecific binding competitor as well as a specific binding competitor, especially preferably, furthermore containing an amplifiable substance library.

In principle, with the selection methods according to the invention, therapeutically or diagnostically functional molecules can be selected against all biological target molecules on cell surfaces. The prerequisite is that a specific ligand, antibody or another binding molecule for the target molecule is already available.

Surprisingly, it has been revealed, that using the method according to the invention, effective binders were found after only about 5 selection rounds. In the status of technology, with other methods, i.e. the so-called SELEX method for the identification of binding nucleic acids from a pool of about $10^{14}$ and more molecules, up to now, a much higher number of selection rounds was necessary. According to the invention, the selection is explicitly not continued until, as in the SELEX method, molecule families are found which, as a rule, requires at least eight to ten selection rounds. On the contrary, according to the invention, after an evidently higher affinity has been reached in the selection pool, which is surprisingly the case after about five selection rounds, the affinity of individual molecules to the target molecule is determined with the same method as that used in preparative selection. This method of procedure rules out the possibility that after too many selection rounds a small group of target molecules (and the molecules binding to them) is selected which represents neither the complete, nor even the larger part of the spectrum of potential target molecules. Unlike the SELEX methods, with nucleic acids, this method (without an extensive search for molecule families) is also particularly important because many target molecules are present in a considerable molecular deficit of several powers of ten in comparison with all other target molecules: A membrane protein with a copy number of 10,000 per cell is not only selected against a few hundred or a few thousand other molecule species of the individual cell surface, but this target molecule, must also be able to be selected efficiently in competition with many other target molecules with a higher number of copies (from a few thousand to a few hundred thousand per cell); this results in the worst case in a molecular surplus of about $10^4$ to $10^5$ of unwanted molecules against the wanted molecule (as the target molecule).

According to the invention, in the case of proteins as the target molecule, the selection is preferably not carried out with isolated target protein but instead with intact cells or cell membranes whereby, according to the invention, an intact cell membrane also includes such which are prepared after the cells have been ruptured e.g. by repeated freezing and thawing. This method ensures that no structural changes through artificial expression e.g. in bacteria and purification of the target protein need to be accepted. Furthermore, it is ensured that the protein still remains in the complex with other proteins.

If a selection is carried out with molecule libraries on living cells or on their surfaces, then an endocytosis of the individual membrane protein, which is being bound as the target molecule, cannot be excluded at temperatures above 4° C. The endocytosis can also be triggered by the binding of the individual molecule or bacteriophage if, at the same time, the interaction with a ligand is imitated. Even when the percentage of proteins which are internalised appears low, it will however add up over the whole time period of the selection, so that after e.g. about three hours after the initial binding of the binding partners from the molecule library and subsequent washing or elution, only a very small percentage of a few percent is left over, i.e. remain as a complex on the cell surface. This is so important because, in contrast with other methods, the molecules or particles which are still bound are regained by liberation from the surface and not by cell digestion and subsequent isolation. Therefore, in order to avoid this problem, in cases where living cells are used, an endocytosis inhibitor such as e.g. cytochalasin B is added.

Ligands which are bound to cell surfaces can also be lost by proteolytic release (Hummel, V., B. A. Kallmann, et al. (2001) J. Neuropathol. Exp. Neurol. 60(4): 320-327.) of the proteins to which they are bound: Thus, in addition to the membrane-bound proteins of the selectin family or the "cell adhesion molecule" (CAM) family (ICAM, VCAM), there are the corresponding soluble proteins (sICAM, cVCAM), which can also be detected in blood (Mukae, H., J. Ashitani, et al. (2003) Respirology 8(3): 326-331). In order to avoid losses of bound molecules in selections against membrane proteins of this class, corresponding protease inhibitors can be added to the corresponding binding and washing solutions.

According to the invention, is thus a method established in which i) surface proteins on mammalian cells, cell membranes and membranes, ii) surfaces of organelles, or cell membranes, and iii) cells in which the target protein, in some cases together with other target molecules, was expressed as membrane protein iv) and molecules as components of an extracellular matrix are accessed using molecule libraries as target molecules for an active substance development. This occurs by binding to the cell, organelle, or membrane or extracellular matrix in the presence of certain additives, washing off of non-bound or weakly bound molecules or particles and separation of those which are still bound through competition with a known ligand, e.g. an antibody present in excess. Subsequently, either (a) the analysis and characterisation of the bound molecules can take place directly; or (b) the analysis and characterisation of the bound molecules follows steps for isolation and amplification (e.g. by cloning); or (c) the method is repeated once again or even several times—whereby the mixture of the bound molecules is used either directly for binding or first after amplification. In this case (case "c"), after the amplification (in vitro or in vivo), the bound volume of the last selection is determined, from this the relative affinity of the individual selection round is estimated and the complete selection procedure is repeated. If an increased binding after at least three to five rounds is observed, individual binding molecules are isolated and their relative affinity is determined. This can be carried out according to the same method as in the actual selection procedure, i.e. by binding with subsequent competition by the same antibody or ligand as well as quantitative determination of the bound volume of the individual molecule; an alternative method here, is e.g. to pursue the binding of the ligand or antibody which was used in the selection procedure, whereby, by adding a defined concentration of the individual binding molecule as the competitor, its binding is inhibited and active molecules are identified.

The separated specific binding molecule, which is either in solution or in suspension, is thus either directly identified by corresponding analysis or is proliferated using an amplification procedure suitable for the chosen amplifiable substance library and subsequently isolated and identified using suitable methods.

A large number of substances can be used as nonspecific binding competitors such as e.g. milk powder, serum proteins such as serum albumin or nucleic acids such as tRNA or yeast RNA. In the method according to the invention, when using living cells as membrane, it has proved to be advantageous to use erythrocytes in addition as nonspecific binding competitors. Alternatively, erythrocyte ghosts (membrane skeletons) or various other cells or their membranes can be used as binding competitors, such as e.g. cell lines of haematopoietic origin, such as lymphoma or leukaemia cells, or HeLa suspension cells, as well as cell organelles such as cell nuclei, mitochondria and others. The prerequisite here, is that the cells, cell membranes or organelles do not carry the target protein of the method being used in their membrane.

According to experience with such selection methods, it is not usually the competing target molecules which are a problem, but rather the nonspecific binding of the substance class of the potential binding molecules which is used (e.g. nucleic acids, proteins). Both can have interactions with, in principle, all biological molecules. On a cell surface, the problem is particularly the large number of hydrogen bridge bindings, which can be made with proteins and particularly with glycosylated proteins or lipids. Whether one can describe these as "specific" or "nonspecific" is unimportant in most cases; however, in the difficult task of selecting on rare proteins on cell surfaces as target molecules, even a weak binding to an excess volume of sugar molecules can make the task too difficult. Therefore, according to the invention, in order to avoid nonspecific cell binding, preferably other cells, here erythrocytes, as nonspecific competitors according to the present invention, are added to the binding solution and to certain washing solutions. This also has the practical advantage that the efficiency of the washing steps, where no erythrocytes were added, can be easily controlled optically by observing the diminishing red colour, and, if necessary, further washing can be carried out. The method enables a selection of highly specific binding RNA molecules from a library after only five rounds.

According to the invention, preferably such molecules are understood as selected target molecules which are present in vivo in or on the cell membrane preferably of mammalian cells, and for which a highly specific ligand such as e.g. an antibody, an aptamer or another ligand already exist. In general, these target molecules are proteins or sugar molecules. There can, however, also be complexes of both substance classes or nucleic acids and their derivatives and other molecules which occur on or in biological membranes.

Of course, this ligand can also be isolated directly before the method is performed.

According to the invention, the selection is performed in an aqueous medium such as buffer systems which are well known to experts in this field, in particular phosphate buffer, HEPES buffer and Tris buffer.

Between steps b) and d) of the method, according to the invention, as defined in claim 1, a washing procedure is carried out. This serves to remove any nonbound material and normally uses the same medium as in steps a) and b), with or without nonspecific binding competitor.

The specific binding competitor used is the specific ligand already mentioned above. Subsequently, out of step e), the selected binding molecule(s) is/are amplified isolated and characterised using a suitable method. These methods depend on the nature of the chosen substance library and are all well-known and obvious for experts. For example, in aptamer libraries, the aptamers are amplified using a PCR reaction. If one uses phage display or related technologies, the selected phage particles are proliferated in bacteria cells, usually *E. coli*.

With synthetic-chemical (combinatorial) libraries, the selected molecules are identified with suitable methods. For example, coding methods are known in the status of technology which, via the covalent docking of the synthetic chemical molecules to (i) carrier particles in the form of a chemical coding (Blackwell, H. E., L. Perez, et al. (2001) Chem. Biol. 8(12): 1167-1182; Clemons, P. A., A. N. Koehler, et al. (2001) Chem. Biol. 8(12): 1183-1195), or to (ii) bacteriophages as biochemical (genetic) coding (Woiwode, T. F., J. E. Haggerty, et al. (2003) Chem. Biol. 10(9): 847-858), allow a later identification of the bound molecules from the molecule library. The advantage of the second method lies in the fact that, due to the coupling to the coded bacteriophages, the complete molecule library, which was obtained by combinatorial synthesis, can be implemented as a "single pool", i.e. a mixture of several hundred (here: 980) chemical substances is used in one single step. Thus complicated logistics are unnecessary which would otherwise be required for binding tests with all substances individually (Fellouse, F. & K. Deshayes (2003) Chem. Biol. 10(9): 783-786).

The expression "native" or "native protein, molecule" is used here to describe such molecules which are present in a conformation and environment which correspond to the in vivo situation so that the full functionality of both the molecule as well as the binding molecules is guaranteed.

In particular, these are molecules on the surface of cells. Also included are recombinant molecules which are expressed by the cell and which are present e.g. on the cell surface, the surface of cell organelles or artificial vesicles and other constructs which imitate the membrane environment.

Suitable endocytosis inhibitors, according to the invention, include for example cytochalasin B, cytochalasin D, cytochalasin E, latrunculin A and B, swinholide A and other substances which block the function of cytoskeletons. A kit of parts, according to the invention, is understood to be a commercially available package containing at least one specific and one nonspecific binding competitor which can also be marketed together with an amplifiable substance library.

EXAMPLES

The following embodiments exemplify the invention without any limiting effect however. Here, using the method according to the invention as representatives for other selection systems, aptamers are selected which bind specifically to IAP and which thus inhibit the apoptosis of cultivated endothelial cells induced by TSP-1. (Freyberg et al., BBRC 2000, 271, No. 3, pages 584-588).

The following overview shows the materials used and their sources (all sources are located in Germany unless otherwise stated):

| Material | Company, Location | Order No. | Comment |
|---|---|---|---|
| Phenol | Carl Roth, Karlsruhe | 0038.1 | TE equilibrated |
| Taq polymerase | Peqlab, Erlangen | 01.1030 | |
| T7 RNA polymerase | MBI-Fermentas, St. Leon-Roth | EP0111 | |
| RevertAid M-MuLV-Reverse transcriptase | MBI-Fermentas, St. Leon-Roth | EP0441 | |

-continued

| Material | Company, Location | Order No. | Comment |
|---|---|---|---|
| ATP, GTP | Carl Roth, Karlsruhe | K045.1 K047.1 | |
| 2'-NH$_2$-UTP | tebu-bio, Offenbach | N-1027 | Manufacturer: TriLink, San Diego, USA |
| 2'-NH$_2$-CTP | | N-1026 | |
| RQ1 DNase I, RNase-free | Promega, Mannheim | M6101 | |
| Chemicals, | Carl Roth, Karlsruhe | | |
| Biochemicals | Merck, Darmstadt; Sigma, Deisenhofen | | |

Synthetic DNA:

primer A:
(SEQ ID NO: 1)
GCGAAGCTTTAATACGACTCACTATAGGGAGACGATATTCGTCCATC primer B:
(SEQ ID NO: 2)
GGTCGAGAATTCAGTCGGACAGCG Lib40:
(SEQ ID NO: 3)
GAATTCAGTCGGACAGCG(N$_{40}$)GATGGACGAATATCGTCTCCC Double distilled water for preparing solutions was treated with diethyl procarbonate (DEPC), 0.01 % (v/v) for 24 hours at 20 to 25° C. and subsequently autoclaved for 60 min 121° C.; it is then called "DEPC-H$_2$O".

Solvents:

| TE buffer | 10 mM Tris HCl, 0.1 mM EDTA, pH 7.6 |
|---|---|
| CI | chloroform/isoamyl alcohol mixture 24:1 (volume/volume) |
| 1xTBE | 90 mM Tris, 90 mM boric acid, 1 mM EDTA |
| 1xPBS + Mg | 130 mM NaCl, 15.4 mM Na$_2$HPO$_4$, 4.6 mM NaH$_2$PO$_4$, 5 mM MgCl2 |
| Wp3E | 65 mM NaCl, 7.7 mM Na$_2$HPO$_4$, 2.3 mM NaH$_2$PO$_4$, 2.5 mM MgCl$_2$, 0.25 mM CaCl$_2$, 12 µg/ml tRNA (yeast), 50% (v/v) erythrocyte suspension |
| Wp3EC | such as Wp3E + cytochalasin B (end concentration 5 µM) |
| WP3 | 130 mM NaCl, 15.4 mM Na$_2$HPO$_4$, 4.6 mM NaH$_2$PO$_4$, 5 mM MgCl$_2$, 0.5 mM CaCl$_2$, 12 µg/ml tRNA (yeast) |
| Wp3T | 130 mM NaCl, 15.4 mM Na$_2$HPO$_4$, 4.6 mM NaH$_2$PO$_4$, 5 mM MgCl$_2$, 0.5 mM CaCl$_2$, 12 µg/ml tRNA (yeast), Tween 20 (0.1% {v/v}) |

Example 1

Construction of a Nucleotide Sequence Bank as PCR-DNA

For the construction of an aptamer bank, a DNA was synthesised by PCR, according to the procedure described by M. Homann and H. U. Göringer {(1999) Nucleic Acids Res., 27 (9), 2006-2014}, with the three described oligonucleotides i.e. a 79 nucleotide-long DNA oligonucleotide as template, called "Lib40", which contained a 40 nucleotide-long segment with a random sequence, called "N40", whereby N represents each of the four nucleotides, A, G, C or T, and two oligonucleotides, which acted as primers for the PCR, called "primer A" and "primer B". A double-stranded DNA is formed with PCR for which, due to the promoter of the T7 RNA polymerase, the "N40"-sequence can be transcribed into RNA. 20 PCR probes were carried out parallel, whereby each PCR probe, in a volume of 200 µl, contained: 160 pmol "primer A", 160 pmol "primer B", 74.2 pmol Lib40-DNA, buffer solution as prescribed by the manufacturer of the enzyme taq-polymerase (Peqlab, buffer "blue")—here with an end concentration of $MgCl_2$ of 1.5 mM—four nucleoside triphosphates dATP, dGTP, dCTP and dTTP—each with 0.25 mM, and 7.5 units of the enzyme taq-polymerase. PCR protocol:.20 sec 94° C., then PCR cycle: 94° C. for 70 sec, 44° C. for 90 sec, 72° C. for 70 sec. Eight cycles were carried out here with subsequent cooling down to 4° C. The purification was performed by phenol extraction, then extraction with CI (chloroform/isoamyl alcohol, 24:1 volume relationship [v/v]), and an ethanol precipitation by adding sodium acetate, pH 5.6, to a concentration of 0.3 M, and the 2.5-fold volume of ethanol p.a. Then incubation took place for at least 30 min at −20° C. with subsequent centrifuging for 25-35 min at 20,000-21,000 g and a temperature of 4-18 °C. After the supernatant had been removed, the precipitate was washed with 70% (v/v) ethanol p.a. The supernatant is dissolved in a total of 100 µl TE buffer and stored at −20° C.

Example 2

Synthesis of the y-amino-RNA

Starting from double-stranded PCR-DNAs (individual PCR probes: for selection round 1: 2.0 to 2.3 nmol DNA from example 1; subsequent selection rounds: 1.0 to 1.3 nmol DNA, from example 5, PCR "P2"; analytical probe: 60 to 70 pmol DNA from second PCR, example 6) which contain the promoter sequence of the T7 bacteriophage (see example 1), the y-amino-RNA is synthesised by the T7 RNA polymerase. Y-amino-RNA is understood as a modified RNA where the pyrimidines (nucleotides U and C) carry an $NH_2$ (amino) group at the 2' position instead of the OH group. The transcription in the presence of ATP and GTP (1 mM of each) as well as the modified nucleotides 2'-$NH_2$-UTP and 2'-$NH_2$-CTP (1 mM of each; modification see above, replacement of the hydroxyl group by an amino group at the 2'-position) takes place by incubation with the commercial T7 RNA polymerase (2 units/µl) at the conditions recommended by the manufacturer and with an additional 2 mM $MgCl_2$, in a volume of 400 µl (selection round 1: 800 µl; analytical probe: 40 µl) at 16° C.±3° C. for 20 to 44 hours. Then the DNA which still remains is digested by adding $MgCl_2$ (increase of the concentration by 2.74 mM) and RNase-free DNase I (end concentration 0.06 units/µl) and incubation at 37° C. for 135 min, whereby 1 unit DNase I is defined as the volume of enzyme which cleaves 1 µg DNA in 50 µl in buffer with 40 mM Tris-HCl, 10 mM NaCl, 6 mM $MgCl_2$, 10 mM $CaCl_2$, (pH 7.9 at 25° C.) completely in 10 minutes at 37° C.

After adding the same volume of TE buffer, the solution is first extracted with phenol and then with chloroform/isoamyl alcohol (24:1—{v/v}). After this, the y-amino-RNA is precipitated with ethanol (see example 1) and, after washing with 70% ethanol, dissolved in 300 µl (selection 1: 1.2 ml; analytical probe: 30 µl) DEPC-$H_2O$. The yield of y-amino-RNA is determined by analysis after separation in a polyacrylamide gel (9.47% (w/v) acrylamide and 0.53% bis-acrylamide, 8 M urea and 1×TBE buffer) in the presence of 1×TBE buffer. The separation of the nucleic acids was carried out at 12 to 16 V/cm for 35 to 45 min. The gel was stained with the fluorescent dye SYBR Green II (Molecular Probes; concentration according to manufacturer's instructions) for 20 min, excited with UV light and the fluorescence in the visible range was analysed.

Example 3

Pre-incubation of the RNA

The y-amino-RNA is used in the probe in a concentration of 150-360 nM; in the pre-incubation solution, the y-amino-RNA concentration is 2.02-fold higher in "1×PBS+Mg" (130 mM NaCl, 15.4 mM $Na_2HPO_4$, 4.6 mM $NaH_2PO4$, 5 mM $MgCl_2$) and tRNA from yeast, 0.3 mg/ml, (volume: selection round 1, 4 ml; from selection round onwards, 2 ml; analytical probe, 300 µl, see below). The pre-incubation is carried out by heating to 92° C. for 1 min and subsequent cooling to 37° C. within 45 min. The solution is then either used directly or stored at −20° C. and thawed before being used further. The pre-incubation is continued by incubation for 20 minutes at 37° C.; then cytochalasin B solution (1 mM in dimethyl sulfoxide; end concentration 10 µM in the binding solution) and an erythrocyte suspension (banked blood) are added in a volume relationship of 1:1 (e.g. 2 ml pre-incubation solution with cytochalasin B+2 ml erythrocyte suspension) and mixed. The resulting binding solution has a volume of 8 ml (selection round 1) or 4 ml (from selection round 2 onwards) (analytical procedure, see below), from which 1 ml each per 75 $cm^2$ culture flask with HUVEC cells is used (see example 4). Before being used further, the solution can be stored at 20 to 30 °C. for a maximum of 10 min, or up to 30 min at 4° C. In the analytical probe (binding test) with individual RNA aptamers, a binding solution consisting of 300 µl of pre-incubation solution (with cytochalasin B) and 300 µl of erythrocyte suspension is used. From the mixture, (binding solution 600 µl) two wells are filled with 300 µl each (see example 4).

Example 4

Selection of y-amino-RNA, and Analytical Binding Test: Binding to Cells and Competition By Antibodies Eukaryotic cells are cultivated according to standard conditions, HUVEC cells are further cultivated in culture flasks with 75 $cm^2$ surface (analytical binding test: HUVEC in 6 well plates) for a further three to five days after reaching confluence (see example 7) and then used in the binding test (two wells are needed for every y-amino-RNA to be tested in the analytical binding test, see below). The volume of washing solution refers in each case to a culture flask or well; after removal of the culture medium, the cells are washed twice with serum-free cell culture medium (IF basal medium, see example 7; 37° C.; volume 5 ml each; analytically: 0.5 ml), then with 1×PBS+Mg solution (3 ml; analytically: 0.4 ml; 18-25° C.), then with 1×PBS+Mg with the addition of 10 µM cytochalasin B (3 ml; analytically: 50 µl; 18-25° C.). After removal of the washing solution, 1 ml each (analytically: 0.3 ml) of the y-amino-RNA erythrocyte-suspension (see example 3, "binding solution" after pre-incubation) is applied to the cells, and while the cells are shaken on a tilting shaker at a frequency of 30/min, they are incubated at 21-30° C. for 60 min, whereby every 10 minutes, the suspension is additionally distributed over the cells by hand by tilting the culture vessel. After the addition of 1.25 ml each (analytically: 0.2 ml) of Wp3, the suspension is removed. The cells are washed successively with the following solutions (the temperature of the washing solution is given in brackets); twice with 1.5 ml each of (analytically: 0.2 ml) Wp3E (4° C.); once with 4 ml each of (analytically: 0.5 ml) Wp3EC for 20 min under shaking (see above; at 21-30° C.); three times with 2 ml each of (analytically: 0.25 ml) Wp3T (21° C.); five times with 4 ml each of (analytically: 0.5 ml) Wp3 (21° C.).

The anti-CD47 antibody "Bric 126" in a concentration of 2 µg/ml in 1×HBS (25 mM HEPES-NaOH pH 7.4, 0.137 M NaCl, 5 mM KCl, 0.7 mM CaCl$_2$, 0.5 mM MgCl$_2$) with 12 µg/ml yeast-tRNA is prepared as the antibody against the selected target IAP (CD47) and 2 ml each is applied (analytically: 0.3 ml, and additionally instead of "Bric 126"—, 0.3 ml with control-antibody mouse IgG) to the cells as competition for the bound y-amino-RNA and incubated for 2 hours at 21-30° C. while shaking on a tilting shaker (see above), whereby, every 15 minutes, the solution is additionally distributed over the cells by tilting the culture vessel. In order to remove the cells, the solution is transferred to Eppendorf vessels and centrifuged for 10 minutes at 900-1,000 g at 12-18° C. The supernatant is removed and precipitated with ethanol (see example 1, here: precipitation for 18-24 hours); the centrifuging is carried out at 20,000-21,000 g and 4-18° C. The precipitate is washed with 70% (v/v) ethanol p.a., dissolved in 50% (m/v) guanidinium isothiocyanate, 25 mM sodium citrate, pH 7.0, extracted with a mixture of phenol and Cl (v/v 1: 1) with subsequent ethanol precipitation of the aqueous phase and centrifuging. The precipitate is washed (see example 1) and then dissolved in 50-110 µl (analytically: 10 µl) H$_2$O; of this, 50-80% are used for the reverse transcription (see example 5).

Example 5

Reverse Transcription of the y-amino-RNA and Amplification of the DNA Copy By PCR (RT-PCR)

Of the two DNA primers, which are used for the synthesis of the double-stranded DNA (see example 1), one contains the DNA sequence of the T7 RNA polymerase promoter. The second primer is used in the reverse transcription for the detection of the RNA by RT-PCR (reverse transcription and subsequent PCR). For this, the purified RNA (see example 4) together with 960 pmol (selection round 1) or 240 pmol (from selection round 2 onwards, and "analytically") of "primer B" is incubated in 110.8 µl (sel. round 1), or 27.7 µl (from sel. round 2 onwards) (analytically, 13.9 µl), heated in a heating block for 1 minute to 65° C. and within 45 min allowed cooled down to 42° C. Then, 5-fold concentrated buffer solution (according to the manufacturer: for enzyme MMuLV Reverse Transcriptase, "Revert-Aid") is added (so that in the probe, as the end concentration, a 1-fold buffer is present) as well as dNTP solution (dATP, dGTP, dTTP and dCTP, each with an end concentration of 1 mM) and 2.4 units/µl of the enzyme Revert-Aid Reverse Transcriptase (MBI Fermentas) making up a total volume of 210 µl (sel. round 1), or 50 µl (from sel. round 2 onwards) (analytically 25 µl) which is mixed and incubated for 30 min at 42° C. and then for 20 min at 48° C. Parallel to this, a probe is carried out with the same concentrations but without the addition of RNA (control "K") in order to be able to detect any unintentional introduction of DNA after the PCR "P1" (see below). After the reaction, the enzyme is inactivated by incubation for 10 min at 68° C. Then, an ethanol precipitation is carried out (with washing of the precipitate; see example 1), and the nucleic acid is dissolved in DEPC-H$_2$O and stored at −20° C.

Subsequently, the following two PCR reactions ("P1" and "P2") are carried out after each other, of which P1 serves to provide the evidence of the affinity of the RNA-pool used in example 4 (through RT-PCR), or, in the analytical probe, identifies specifically binding aptamers (example 4, "analytical") after the RT-PCR, due to an increased DNA volume in the case of the specific antibody (here Bric 126) in comparison with the control antibody (see below, "analytical"), whereby a PCR reaction and subsequent gel electrophoresis are carried out (see example 6). A defined portion (25-80%) of the solution (after reverse transcription) or of the control solution K, in a volume of 400 µl (analytical probe: volume 40 µl), at the buffering conditions recommended by the manufacturer (here: "PCR buffer blue", Peqlab, Erlangen) with dNTP solution (see above, concentration in each case of 300 to 320 µM) as well as the DNA primers "primer-A" and "-B", 320 pmol of each (analytical: 40 pmol of each) and the enzyme taq-polymerase, 5 to 15 units (analytical: 3.5 units) are mixed in 500 µl PCR Eppendorf vessels and a PCR reaction ("P1") is performed under the following conditions (see example 1): 20 sec 94° C., then cycle: a) 94° C., 1 min; 44° C., 1 min and 30 sec; 72° C., 1 min and 10 sec; a total of 25 cycles, then cooling to 4° C. before proceeding. After the defined cycle number, e.g. 6, 9, 12, 15 and 25 cycles, samples of 4 µl each are taken (analytical probe: only 18 cycles, after this, only one sample of 4 µl) which are then analysed with gel electrophoresis (see below). The samples were taken after interrupting the program at the end of each cycle 10 seconds before the end of the 72° C. phase. Here, alternatively, the samples are taken without removing the sample tubes; or all probes are placed in an ice bath, the samples are taken and the probes are replaced in the PCR cycler; subsequently, the program is continued until completion. The analysis of the synthesised volume of DNA after the given cycles is carried out after separation of the samples in a polyacrylamide gel with subsequent SYBR-green staining (see example 2). Thus, at this point, the volume of y-amino-RNA bound to the cell can be determined by quantitative RT-PCR in every selection round. If the increase of the RNA volume is shown by the appearance of PCR-DNA, already after e.g. the 6$^{th}$ PCR cycle, instead of after the 8$^{th}$ or 9$^{th}$ in earlier selection rounds, then, an accumulation of stronger binding y-amino-RNA must have taken place. After a further PCR ("P2") for amplification of the DNA, either a second selection round then follows (synthesis of y-amino-RNA, binding to cells with selection, RT-PCR), or individual molecules are characterised by cloning and analysis of the affinity and sequences of these clones (see example 6). The preparative PCR ("P2") is carried out under similar conditions to those for PCR "P1" (primer 0.8 µM each), with the following differences: 1) in a total volume of 2 ml, which is distributed over 10 probes each with 200 µl (analytically: 150 µl); and 2) the number of cycles is limited to 12 (analytically: 20 cycles). The analysis of the PCR is carried out as above after the last cycle by gel electrophoresis. After extraction with phenol and CI and an ethanol precipitation of the DNA (see example 1), the transcription is carried out with T7 RNA polymerase for the synthesis of the y-amino-RNA (see example 2).

Example 6

Cloning and Sequencing of DNA Copies of the Selected y-amino-RNA and Analysis of Their Affinity The cloning of PCR fragments after round 5 of the selection of y-amino-RNA and RT-PCR was carried out according to the known methods (Heyman, J. A., J. Comthwaite, et al. (1999) Genome Res. 9(4): 383-392; Shuman, S. (1994) J. Biol. Chem. 269(51): 32678-32684). Plasmid DNA was isolated from individual clones (Bimboim, H. C. and J. Doly (1979) Nucleic Acids Res. 7(6): 1513-1523), and PCR reactions were carried out with the plasmid DNAs, and after this, y-amino-RNA was synthesised with which binding tests and functional tests were carried out. For this, first of all PCR- DNA was prepared in two steps (see example 5, corresponding to PCR "P2", analytically). First PCR: volume 50 μl; DNA template, in each case plasmid DNA of the individually isolated clones (plasmid mini preparation of 1 ml bacterial suspension, of which 4% was used in the PCR); 18 cycles. Second PCR: volume 150 μl; DNA template, PCR-DNA from the first PCR, 14 cycles. The RNA synthesis then follows (see example 2, "analytical"), preincubation (example 3, "analytical") and binding (example 4, "analytical"). Then the reverse transcription is carried out (example 5, "analytical") as well as a PCR according to the following procedure: In accordance with the description in example 5 ("P1"), PCR reactions were each performed in reaction volumes of 40 μl, whereby parallel one reaction each were performed with samples from the two competition reactions with the antibody Bric 126 and the control antibody respectively (see example 4). 25 PCR cycles were performed, whereby samples of 4 μl each were taken after 7, 10 and 25 cycles (example 5) and analysed by gel electrophoresis (see example 2). A specific binding to the target protein CD47 was demonstrated by the increased volume of PCR-DNA after competition from the Bric126 antibody in comparison with the control antibody. Furthermore, functional tests for their anti-apoptotic action were performed with the individual RNAs ("aptamers")(see examples 7-10). Individual clones were chosen and the associated plasmid DNAs were sequenced. The sequence of y-amino-RNAs was derived from the DNA sequence obtained.

Example 7

Cultivation of Human Endothelial Cells From Umbilical Veins (HUVEC)
Solutions (Sterile):
Culture medium: IF Basal Medium+15% (v/v) NCS, 5 μg/ml transfenin, 5 μg/ml heparin, 0.7 μg/ml FGF, 2 mM L-glutamine [IF Basal Medium: 1:1-mixture of Iscove's Modified Dulbecco Medium (IMDM) and Ham's F12, both from Life Technologies, Paisley (Great Britain)]
NCS: New-born calf serum (Sebak, Aidenbach)
FGF: Fibroblast growth factor (own production, partially purified from porcine brain)
Materials:
Cell culture vessels, gelatin-coated
Experimental Procedure:
The cultivation of HUVEC is carried out in gelatin-coated culture vessels at 37° C. in a 5% $CO_2$ and steam-saturated air atmosphere. The culture medium is changed every 2-3 days; at confluence the cells are passaged with a separation rate of 1:3 to 1:5. HUVEC grow strictly contact-inhibited and form single-layer cell lawns with the typical cobblestone morphology. At confluence, the cultures reach cell densities of $4-9\times 10^4$ cells/cm$^2$. For apoptosis examinations, HUVEC cultures of the passages 1-4 are used exclusively.
Coating of Culture Vessels:
Solutions (Sterile)
Gelatin solution, 1% (w/v) in Milli-Q water
Suspend 1 g of gelatin (cell culture tested) in 100 ml Milli-Q water, dissolve by autoclaving for 20 min at 121° C. and 2 bar and store at room temperature.
PBS (140 mM NaCl, 3 mM KCl, 8 mM $Na_2HPO_4$, 1.5 mM $KH_2PO_4$)

8 g/l NaCl
0.2 g/l KCl
1.44 g/l $Na_2HPO_4 \times 2\ H_2O$
0.2 g/l $KH_2PO_4$
The prepared solution is autoclaved for 20 min at 121° C. and 2 bar and stored at room temperature. The pH value is measured and lies between 7.2 and 7.4.
Materials:
Cell culture vessels
Experimental Procedure:
Culture vessels are coated with gelatin for the cultivation of adherently growing cells. The bottoms of the cell culture vessels are covered with sterile gelatin solution and the vessels are left to stand for 15 minutes at room temperature. The gelatin solution is suctioned off. The cell culture vessels are washed once with PBS and can then be used.
Subcultivation of Adherent Cells
Solutions (Sterile):
PBS
Trypsin/EDTA (0.05% (w/v)/0.02% (w/v))
0.1 ml trypsin stock solution
0.05 ml EDTA stock solution
Fill up to 50 ml with sterile PBS and store in portions of 10 ml at −20° C.
Materials:
Cell culture vessels, gelatined
Experimental Procedure:
All cell types are detached from the culture surface with trypsin/EDTA solution. The culture medium is removed by suction. The bottom of the culture vessel is briefly washed with PBS and then covered with trypsin/EDTA solution (~1 ml for a 25 cm$^2$ culture flask). The enzyme solution is immediately suctioned off again so that a thin liquid film remains on the cells. The cells are left to stand at room temperature for 1-10 min and the detachment of the cells is observed under the microscope. The detachment of the cells can be accelerated by gently tapping the culture vessel on the edge. The cells are transferred to fresh culture medium, if required counted, and then seeded out in new culture vessels.

Example 8

Determination of the Apoptosis Rate By Staining Apoptotic Cells With DAPI
DAPI belongs to the indole dyes group and provides a selective DNS stain. The stain is excited at 340-360 nm with an emission maximum of 480 nm. The substance is used for apoptosis examinations [compare: Cohen et al. (1993) Immunology Today, 14 (3), 126-130].
Morphological Evaluation:
Solutions:
PBS
Formaldehyde solution
4% (v/v) formaldehyde in PBS
DAPI solution (Molecular Probes, Leiden, Netherlands)
2 μg/ml DAPI in methanol
Materials:
Petri dish (35 mm) or 24 well plate with HUVEC cell in culture
Experimental Procedure:
The culture supernatant of a Petri dish or 24 well plate is suctioned off. The cell-lawn is fixed for 15 minutes with 1 ml formaldehyde solution cooled on ice, washed twice with 2 ml PBS. 0.5 ml DAPI solution is added for 15 minutes, then washed again with PBS and evaluated under the fluorescence microscope. This work is carried out with a UV filter set and a 20× or 40× objective. 500-1000 cells are chosen at random and the number with apoptotic nuclei are counted.

The apoptosis index is calculated according to the following formula:

Apoptosis index [%]=number of apoptotic cells/total cell count×100

Example 9

Testing System for Anti-apoptotically Active Aptamers

The cells are cultivated in the manner described in example 7. The cells are seeded in appropriate culture vessels (e.g. 24 well plate/0.5 ml per well) and after reaching complete confluence they can be used for the actual test.

The induction of apoptosis is carried out by TSP 1, which endothelial cells produce and secrete themselves, and which enriches itself in the culture medium (autoconditioning of the culture medium).

Examinations are carried out to establish the influence of the various aptamers on the apoptosis rate of endothelial cells. For these, the aptamers, which are dissolved in DEPC-treated double distilled water (example 6), are diluted in the in the culture medium for HUVEC (example 7) and used at the given concentrations. Culture medium without any aptamers or inhibitors whatsoever is used as the positive control.

The medium with the aptamers is added to the cells and incubated for three days under culture conditions (example 7). After 36 hours, the culture medium/culture medium with aptamers is changed once.

Subsequently, the cells, as described in example 4, are stained with DAPI to determine the apoptosis rate and the apoptosis index is calculated with the given formula.

The clearly apoptosis-inducing action of the autoconditioned medium in the case of the positive control, and the reduced apoptosis in the case of the inhibition control, demonstrate the success of the test as an internal control.

Example 10

Identification of Anti-apoptotically Active Aptamers Using the Method According to the Invention.

The cells are cultivated in the manner described in example 3. The cells are seeded in appropriate culture vessels (e.g. 24 well plate/0.5 ml per well) and after reaching complete confluence they can be used for the test according to example 9. The following samples are prepared:

(K) Culture medium (autoconditioned medium, basis rate of apoptosis, control), (1) Culture medium+aptamer 89, concentration: 150 nM (2) Culture medium+aptamer 89, concentration: 300 nM (3) Culture medium+aptamer 82, concentration: 150 nM (4) Culture medium+aptamer 82, concentration: 300 nM After 72 hours of incubation under culture conditions, the cells are fixed, stained with DAPI, and examined morphologically under a fluorescence microscope. The apoptotic cell count and the total cell count are determined and the apoptosis index is calculated (percentage of apoptotic cells).

TABLE 1

The following aptamers were tested:

| Sample No. | Aptamer designation Concentration | Apoptosis index [%] | Inhibition index [%]* |
|---|---|---|---|
| K | Control | 3.59 ± 0.54 | — |
| (1) | 89.150 nM | 0.17 ± 0.15 | 95.24 |
| (2) | 89.300 nM | 0.16 ± 0.14 | 95.65 |
| (3) | 82.150 nM | 1.22 ± 0.27 | 66.03 |
| (4) | 82.300 nM | 0.74 ± 0.19 | 79.32 |

*100% = no further apoptosis determinable; 0% = no effect = control

---

The invention claimed is:

1. Method for the manufacture of specific binding molecules against selected target molecules, comprising the steps of
(a) contacting a substance library containing potential binding molecules with the target molecules,
(b) adding to the substance library of (a) a non-specific binding competitor selected from the group consisting of cells, cell membranes and cell organelles, wherein the non-specific binding competitor does not carry the target molecule,
(c) washing the substance library of (b),
(d) adding and incubating a specific binding competitor for the selected target molecule with at least about a 10-fold higher concentration than the dissociation constant $K_D$ (M) of the pair consisting of specific binding competitor and target molecule in the substance library whereby the specific binding molecule is detached, and
(e) isolating the detached specific binding molecule.

2. Method according to claim 1, wherein the substance library is an amplifiable substance library selected from the group consisting of nucleic acid libraries, phage display-libraries, antibody libraries, peptide libraries, and synthetic-chemical libraries.

3. Method according to claim 1, comprising carrying out steps a) and b) simultaneously.

4. Method according to claim 1, wherein the non-specific competitor is chosen from the group consisting of erythrocytes, erythrocyte ghosts (membrane skeletons), cell lines of haematopoietic origin, HeLa suspension cells, and cell organelles, and which do not carry the target molecule in their membrane.

5. Method according to claim 2, comprising carrying out steps a) to e) sequentially, wherein from the second round onwards, the binding molecules obtained in step e) are used in step a) instead of the amplifiable library.

6. Method according to claim 2, wherein the library is an aptamer library.

7. Method according to claim 1, wherein the target molecules which are present are native.

8. Method according to one claim 1, comprising in step a) adding an endocytosis inhibitor in sufficient volume in order to inhibit the endocytosis.

9. Method according to claim 1, wherein the selected target molecule is a membrane-bound molecule of which a soluble form is also known, and comprising adding a proteinase inhibitor during step (a).

10. Method according to claim 1, wherein the specific binding competitor is selected from the group consisting of antibodies and their fragments, aptamers, ligands of the target molecule, and low-molecular competitors.

11. Method according to claim 10, wherein the specific binding competitor binds to a clinical or diagnostic surface molecule of interest.

12. Method according to claim 1, wherein said concentration is at least 100 fold higher than the dissociation constant.

13. Method according to claim 1, wherein said concentration is at least 1000 fold higher than the dissociation constant.

14. Method according to claim 5, wherein steps a) to e) are carried out sequentially three to five times.

15. Method according to claim 7, wherein the target molecules are bound on the surface of a cell membrane or in extracellular matrix.

16. Method according to claim 15, wherein the target molecules in step (a) are bound on a cell membrane or are bound on intact cells.

17. Method according to claim 8, wherein the endocytosis inhibitor is cytochalasin B in a concentration of 1 µM to 10 µM.

18. Method according to claim 10, wherein the surface molecule is Integrin-associated protein (IAP) or alpha-V Beta-3 (αvβ3).

19. Method according to claim 1, further comprising amplifying the detached specific binding substance of step (e) using a method which is suitable for the selected substance library.

* * * * *